United States Patent [19]

Keaton

[11] Patent Number: 5,036,865
[45] Date of Patent: Aug. 6, 1991

[54] SLEEPWEAR

[76] Inventor: Powell J. Keaton, 5157 Mantlewood La., Kernersville, N.C. 27284

[21] Appl. No.: 532,797

[22] Filed: Jun. 4, 1990

[51] Int. Cl.$^5$ .............................................. A61F 5/00
[52] U.S. Cl. ................................... 128/848; 128/871
[58] Field of Search .................. 2/114; 128/848, 871; 600/26, 27

[56] References Cited

U.S. PATENT DOCUMENTS

| 876,491 | 1/1908 | Rohwer | 128/848 X |
|---|---|---|---|
| 898,379 | 9/1908 | Liebhardt | 128/848 X |
| 2,304,235 | 6/1941 | Boots | 128/848 X |
| 2,999,232 | 9/1961 | Wilson | 128/848 X |
| 4,748,702 | 6/1988 | Sandler | 128/848 X |

FOREIGN PATENT DOCUMENTS

| 3322571 | 4/1984 | Fed. Rep. of Germany | 128/848 |
|---|---|---|---|
| 0358878 | 9/1931 | United Kingdom | 128/848 |

Primary Examiner—Robert A. Hafer
Assistant Examiner—Kerry Owens

[57] ABSTRACT

Sleepwear includes a sensor on the back thereof whereby the wearer, in lying in a supine posture will receive a signal therefrom causing him to awaken or turn from said supine posture. Sleepwear may be in the form of a T-shirt having a pair of pockets for containing a mechanical or electrical sensor therein.

16 Claims, 2 Drawing Sheets

SLEEPWEAR

BACKGROUND OF THE INVENTION

1. Field Of The Invention

The present invention pertains to sleepwear and specifically to sleepwear configured to prevent the wearer from inadvertently turning to lie on his or her back as may occur during a prolonged rest period, or when asleep.

2. Description Of The Prior Art And Objectives Of The Invention

Sleepers in a supine posture oftentimes snore or make other audible sounds which can be heard and are disturbing or distracting to a spouse or other nearby sleepers as may occur in a hospital ward, army barracks or the like. When confronted with a snoring husband, a wife may have to frequently nudge the husband in an effort for him to readjust his sleeping position so the snoring will cease. Snoring generally occurs as the sleeper lies in a supine position and rarely occurs when the sleeper is in a side, face-down (prone) or fetal posture. Also, normally healthy persons sometimes develop back sores or rashes which are irritated during sleeping hours if the person, while sleeping heavily, turns onto his back and remains so positioned for extended periods. In view of the disadvantages and problems associated with certain persons in reverting to sleeping on their backs, the present invention was conceived and it is an objective of the present invention to provide apparatus which will make a supine sleeping posture uncomfortable for the user.

It is also an objective of the present invention to provide sleepwear which will sufficiently annoy the user, even during deep sleep, if he turns to a supine posture.

Still another objective of the present invention is to provide sleepwear in the form of a T-shirt which includes a sensor on the back thereof which will generate a signal which will sufficiently disturb the wearer preventing him or her from remaining in a supine posture when the sensor is activated.

It is yet another objective of the present invention to provide sleepwear having a pair of pockets on the back side with each of said pockets containing a resilient or other sensor.

Various other objectives and advantages of the present invention become more apparent to those skilled in the art as a more detailed description is presented below.

SUMMARY OF THE INVENTION

The aforesaid and other objectives are realized by providing sleep apparel in the form of a shirt having a sensor mounted on the back thereof. The sensor may include an electromechanical plunger which is activated if the wearer rolls onto his back during sleep thereby generating an audible signal to awaken the user, or it may consist of a resilient ball positioned in a pocket on the back of said shirt proximate a shoulder blade whereby the resilient ball causes sufficient discomfort when lied upon whereby the sleeper will awaken or at least will turn to a prone or other position to eliminate the annoyance created.

DESCRIPTION OF THE PREFERRED EMBODIMENT

Figure 1:
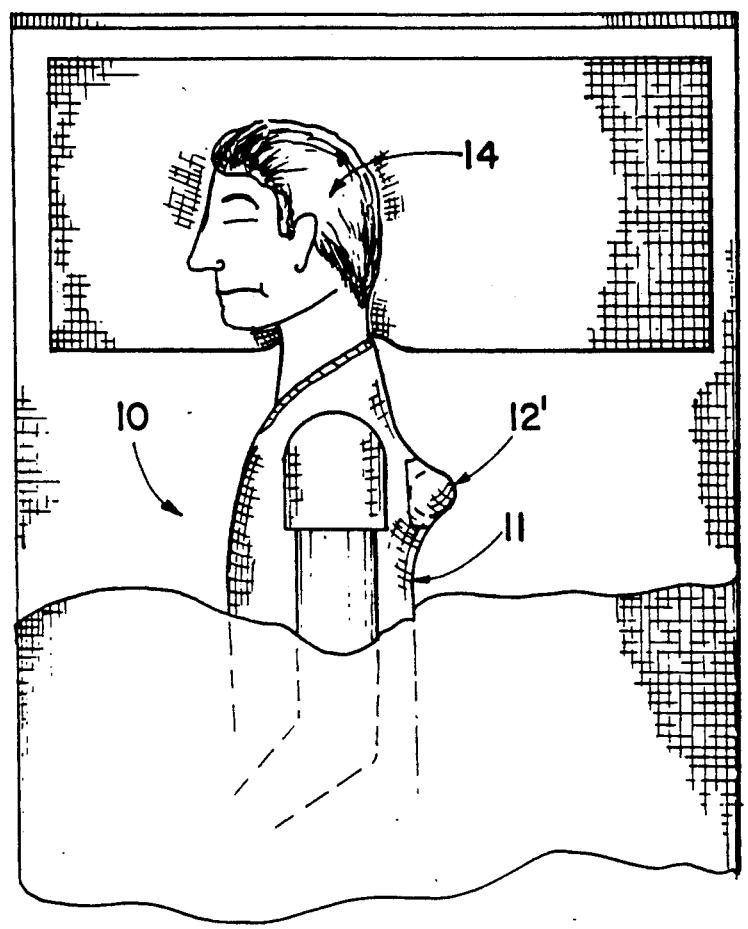
FIG. 1 demonstrates a wearer of the apparatus of the invention sleeping in side fashion.
Figure 2:
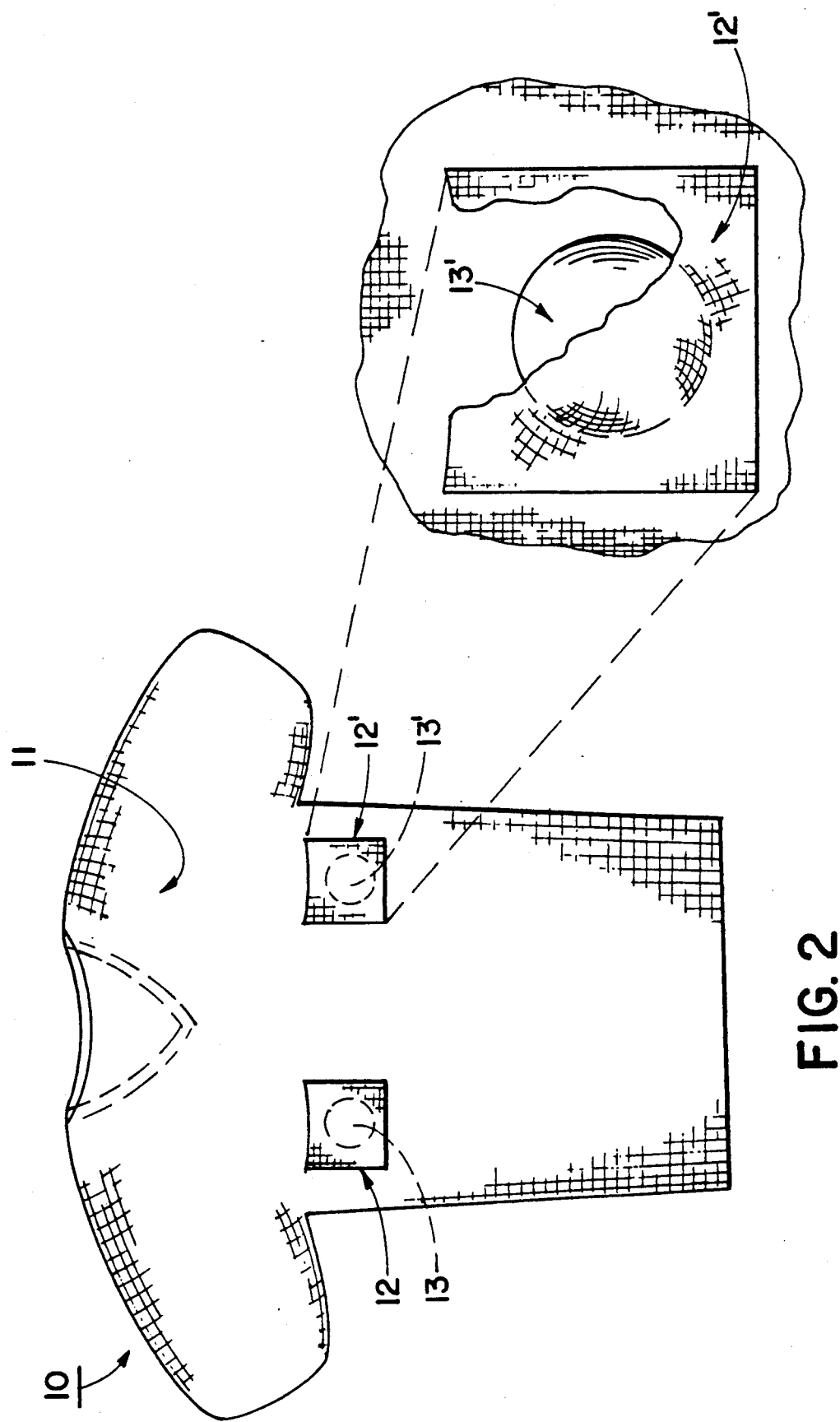
FIG. 2 illustrates the back of a shirt embodiment of the invention having a pair of pockets containing resilient sensors therein.

The preferred form of the invention is illustrated in FIGS. 1 and 2 whereby a T-shirt includes a pair of back pockets positioned proximate the right and left shoulder blades of the wearer. The pockets contain a resilient synthetic ball which, if the wearer turns onto his or her back during sleep, the resilient balls compress and press against the back of the sleeper to annoy the sleeper sufficiently so that he or she will return to a side position as shown in FIG. 1, or to a fetal position or prone position to relieve the annoyance created.

DETAILED DESCRIPTION OF THE DRAWINGS AND OPERATION OF THE INVENTION

For a more complete understanding of the invention and its operation, turning now to the drawings, FIG. 2 illustrates the invention in the form of sleepwear 10 which comprises a cotton T-shirt having a back side 11 with laterally spaced apart pockets 12, 12' attached thereto. Within pockets 12 and 12' respectively are mechanical sensors in the form of resilient balls 13, 13'. The pockets are so placed to avoid direct sensor pressure against the spinal region. It has been found that balls having a relatively lightweight and high resiliency may be used such as tennis balls, racket balls or the like. It would of course be understood by those skilled in the art that various shapes other than spherical could be employed as desired and the exact resiliency and size can also be varied.

In FIG. 1, male sleeper 14 is shown resting on his side whereby ball sensor 13' (not seen in FIG. 1) but positioned in pocket 12' and ball sensor 13 positioned in pocket 12 (also not shown in FIG. 1) will not signal or annoy sleeper 14 as he remains in this position. In the event sleeper 14 rolls or turns to a supine position, sensors 13 and 13' will then signal sleeper 14 as they press against his back at approximately the left and right shoulder blade positions thereby annoying him and causing him to revert to a more comfortable position such as to a side position as illustrated in FIG. 1.

Figure 3:
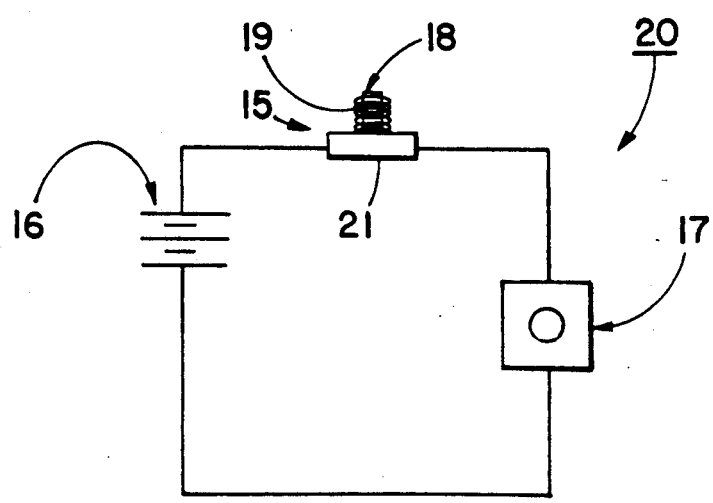
FIG. 3 depicts another sensor embodiment comprising electrical circuitry.

More sophisticated sensor apparatus 20 which can be used is shown in FIG. 3 whereby electrical switch 15 is powered by battery 16 and is connected to a conventional audible/vibrating alarm device 17. Switch 15 provides a means to signal sleeper 14 such as by an audible signal, by vibrating or both. As further shown in FIG. 3, switch 15 includes plunger 18 which is resiliently mounted by coil spring 19. When sensor apparatus 20 is positioned on the back of sleeper 14 as seen in FIG. 1, such as by affixing apparatus 20 within pockets 12, 12', if sleeper 14 turns to lie on his back, plunger 18 is depressed, touching contact 21 and delivering an electrical signal to alarm device 17 which may, as explained above, vibrate or generate an audible signal, or both. The signal so generated will thereby awaken the sleeper and cause him to turn from a supine to a side or prone sleeping posture. Males, females, adults or children may all benefit the invention as herein described.

It has been found that sleepwear 10 as described above will teach a sleeper to remain in a side or frontal sleeping posture and as such does not have to be worn other than periodically in order to receive benefits therefrom. Hence, a sleeper may wear such sleepwear for a week or two and during the third week the user can sleep without, yet he will still remain in other than a supine sleeping position after having "learned" the consequences of receiving the irritating signal from the particular sensor employed.

The illustrations and examples provided herein are for explanatory purposes and are not intended to limit the scope of the appended claims, it being understood that many types and shapes of sensors could be developed and used, depending on a multitude of factors.

I claim:

1. Apparatus for a person to prevent the person from lying in a supine position comprising: wearing apparel having a front and a back, a pair of sensors, said sensors positioned on the back of said apparel, said sensors spaced apart for contact with the back of the wearer on different sides of the spinal region and positioned at approximately the shoulder blades of the wearer whereby in the event the person attempts to lie on his back the sensors will signal the person allowing the person to change positions.

2. Apparatus as claimed in claim 1 wherein said wearing apparel comprises a shirt.

3. Apparatus as claimed in claim 1 wherein said shirt comprises a T-shirt.

4. Apparatus as claimed in claim 1 wherein said sensors each comprise a resilient member.

5. Apparatus as claimed in claim 4 wherein each of said resilient members comprise a ball.

6. Apparatus as claimed in claim 2 wherein said shirt comprises a pair of pockets for receiving said sensors.

7. Apparatus as claimed in claim 1 wherein each of said sensors comprise an audible alarm.

8. Apparatus as claimed in claim 1 wherein each of said sensors comprise a vibrator.

9. Sleepwear comprising: a shirt, said shirt having a back, a pair of sensors, said sensors attached to said shirt back, each sensor positioned to contact the wearer's back on opposite sides of the spinal region proximate a shoulder blade, said sensors for delivering a signal to the wearer in the event the wearer attempts to lie in a supine position.

10. Sleepwear as claimed in claim 9 wherein said shirt comprises a T-shirt.

11. Sleepwear as claimed in claim 1 wherein each of said sensors comprise a resilient member.

12. Sleepwear as claimed in claim 11 wherein each of said sensors comprise a resilient ball.

13. Sleepwear as claimed in claim 9 wherein one of said sensors comprise electrical circuitry.

14. Sleepwear as claimed in claim 13 wherein said electrical circuitry comprises an audible alarm.

15. Sleepwear as claimed in claim 9 wherein said shirt back comprises a pair of pockets, said pockets for receiving said sensors.

16. Sleepwear to prevent the wearer from remaining in a supine posture comprising: a shirt, said shirt comprising a back, a pair of pockets, said pockets positioned on said shirt back and laterally spaced apart on opposite sides of the spinal region of the wearer so each sensor is positioned approximately over a shoulder blade, a pair of resilient balls, said balls contained within said pockets whereby the user, upon attempting to obtain a supine posture will be discomforted by the balls pressing against the wearer's back and will vacate said supine attempt.

* * * * *